United States Patent [19]

Stadnick et al.

[11] Patent Number: 4,567,039

[45] Date of Patent: Jan. 28, 1986

[54] HAIR CONDITIONING COMPOSITION AND METHOD

[75] Inventors: Richard P. Stadnick, Blauvelt, N.Y.; Richard W. Schnetzinger, Hightstown, N.J.

[73] Assignee: Revlon, Inc., New York, N.Y.

[21] Appl. No.: 660,158

[22] Filed: Oct. 12, 1984

[51] Int. Cl.$^4$ .................. A45D 7/00; A61K 7/06; A61K 7/13

[52] U.S. Cl. ........................ 132/70; 8/405; 8/406; 424/70

[58] Field of Search ............. 424/70, 184; 252/49.6

[56] References Cited

U.S. PATENT DOCUMENTS

| | | | |
|---|---|---|---|
| 3,560,385 | 2/1971 | Roth | 252/49.6 |
| 3,624,120 | 11/1971 | Yetter | 424/184 |
| 3,730,701 | 5/1973 | Isquith et al. | 71/67 |
| 4,254,270 | 3/1981 | Kötzsch et al. | 424/184 |
| 4,282,366 | 8/1981 | Eudy | 424/184 |
| 4,342,742 | 8/1982 | Sebag et al. | 424/184 |
| 4,394,378 | 7/1983 | Klein | 424/184 |
| 4,406,892 | 9/1983 | Eudy | 424/184 |
| 4,450,152 | 5/1984 | Ona et al. | 424/184 |

FOREIGN PATENT DOCUMENTS

| | | | |
|---|---|---|---|
| 2542338 | 3/1977 | Fed. Rep. of Germany | 424/70 |
| 2912484 | 10/1980 | Fed. Rep. of Germany | 424/184 |
| 2912485 | 10/1980 | Fed. Rep. of Germany | 424/184 |
| 0066506 | 5/1980 | Japan | 424/184 |
| 7213199 | 4/1973 | Netherlands | 424/184 |

*Primary Examiner*—Dale R. Ore

[57] ABSTRACT

Disclosed is a hair conditioning composition comprising an organosilicon quaternary ammonium salt in an aqueous/organic solvent. Upon application, the composition imparts long-lasting conditioning to hair.

12 Claims, No Drawings

HAIR CONDITIONING COMPOSITION AND METHOD

BACKGROUND OF THE INVENTION

1. Field of the Invention

This invention relates to hair conditioning compositions. More particularly, this invention relates to hair conditioning compositions containing certain organosilicon quaternary ammonium halides that impart long-lasting or "permanent" conditioning effects to hair.

2. Description of the Prior Art

Hair is generally degraded to varying extents by the action of such treatments as bleaching, permanent waving and dyeing and also by the action of atmospheric agents. As a result, the hair is difficult to comb out and to style and does not readily retain an appealing style, mainly due to the fact that the hair is lacking in strength and springiness.

To overcome these difficulties, compositions, which are marketed for home and beauty shop use, are characterized as rinses and conditioners which are designed to impart softness or smoothness of feel, luster, body, manageability, combability, elasticity and an overall appealing appearance to the hair.

Conditioning of hair is, in general, achieved by effecting a deposit on the hair of a film of a character such as serves to impart to the hair one or more of the above-stated properties. Hair conditioning compositions are marketed in various forms, such as aqueous or aqueous-alcoholic solutions, lotions, dispersions and creams.

Among the hair conditioning products which have heretofore been known and some of which have been used commercially to a substantial extent are those of the type which contain cationic agents, generally of the quaternary ammonium type. Cationic agents are known generally to be substantive to the hair and therefore, a film or deposit is formed on the hair shafts by adsorption due to ionic attraction between the cationic agent and the keratinous material of the hair. The character and the amount of such film as is formed and deposited on the hair influence the properties and characteristics of the hair.

The foregoing hair conditioning compositions are reasonably effective in imparting to the hair at least some of the properties and characteristics of the nature described above. However, their conditioning effect on hair is short, generally lasting until the hair is washed/shampooed. In addition, the desired conditioning properties and characteristics imparted to the hair by these conditioners are greatly reduced by unfavorable atmospheric conditions such as the presence of particulate matter and high relative humidity in the air. It is believed that the ionic attraction between the cationic agent and hair keratin is weakened by these conditions resulting in decreased substantivity of film on the hair. As a result, to maintain the hair in the desired well-conditioned form, frequent application of hair conditioners are required.

The present invention is based on the discovery that certain organosilicon quaternary ammonium salts bond to the hair with a force stronger than ionic bonds thereby imparting permanent or long-lasting conditioning to hair.

Certain silicon containing quaternary ammonium halides are known for their antimicrobial and antifungal activity. As such, these compounds have been used on fabrics and other surfaces to prevent and/or inhibit the growth of micro-organisms (see for example, U.S. Pat. No. 4,406,892).

SUMMARY OF THE INVENTION

In accordance with the present invention, a hair conditioning composition is provided which comprises 0.1% w/v to 15% w/v of an organosilicon quaternary ammonium salt of the formula

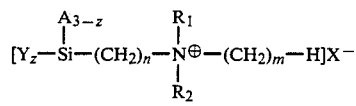

wherein

Y is a hydrolyzable radical or hydroxy,

X is a halogen, preferably chlorine, or other negative species such as sulfate, phosphate and carbonate;

$R_1$ is an alkyl radical of 1 to 4 carbon atoms such as methyl, ethyl, propyl, isopropyl, butyl or isobutyl, and preferably methyl;

$R_2$ is an aliphatic radical of 1 to 4 carbon atoms such as methyl, ethyl, propyl, isopropyl, butyl or isobutyl, or an aromatic radical of 6 to 8 carbons such as benzyl or ethyl benzyl;

A is an aliphatic radical of 1 to 4 carbons or an aromatic radical of 6 to 8 carbons;

n is 1 to 6;

m is 1 to 18; and z is 2 to 3 in an alkaline buffered aqueous/organic vehicle.

Supplemental agents may and, generally, are desirably included in the hair conditioning compositions such as thickeners or viscosity builders, lubricants, preservatives, perfumes, emulsifiers and coloring agents.

The process of conditioning the hair comprises: cleaning the hair, such as by shampooing; applying a sufficient amount of the composition of the present invention to saturate the hair therewith, such as by submerging the clean hair in the composition or applying the composition with an applicator; working it into the hair with the fingers and a comb; allowing sufficient time for swelling and penetration of the active compound into the hair, rinsing the hair with tap water; followed by blow drying with hot air.

DETAILED DESCRIPTION OF THE INVENTION

Referring to the formula of the organosilicon quaternary ammonium salts, the following should be noted.

Hydrolyzable radicals include: alkoxy groups containing up to 4 carbon atoms, such as methoxy, ethoxy, isopropoxy, propoxy and butoxy; and halogens such as chlorine, bromine and iodine, and other negative ionic species as well.

Examples of compounds contemplated for use in the present invention include:

hexadecyldimethyl[3-(triethoxysilyl)propyl]ammonium chloride, hexadecyldimethyl[3-(trimethoxysilyl)propyl]ammonium chloride, octadecyldimethyl[3-(trimethoxysilyl)propyl]ammonium chloride, stearylmethylbenzyl[3-(triethoxysilyl)propyl]ammonium chloride, stearylmethylbenzyl[3-(trimethoxysilyl)propyl]ammonium chloride, stearylmethylethylbenzyl[3-(triethoxysilyl)propyl]ammonium chloride, stearylmethylethylbenzyl[3-(trimethoxysilyl)propyl]ammonium chloride, tetradecyldimethyl[3-(triethoxysilyl)propyl]ammonium chloride, tetradecyldimethyl[3-(trimethoxysilyl)propyl]ammonium chloride, N-triethoxysilylpropyl-N,N,N-trimethylammonium chloride, N-trimethoxysilylpropyl-N,N,N-trimethylammonium chloride Compounds of the present invention are available commercially or can be prepared by art-recognized methods. For example, octadecyldimethyl[3-(trimethoxysilyl)propyl]ammonium chloride, and N-trimethoxysilyl N,N,N-trimethyl propylammonium chloride and tetradecyldimethyl[3-(trimethoxysilyl)propyl]ammonium chloride are commercially available from Petrarch Systems, Inc., Bristol, PA. Other organosilicon quaternary ammonium salts of the present invention can be readily prepared utilizing procedures described in U.S. Pat. Nos. 3,560,385 and 3,730,701. In general, compounds of the stated formula can be readily synthesized by heating at reflux temperature in a polar solvent such as methanol, ethanol and acetone, an excess of an amine of the formula:

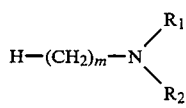

wherein $R_1$, $R_2$ and m are as above-defined, with a silane quaternizing agent of the formula:

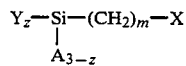

wherein

X, Y and n are as above-defined, and z is 2 or 3.

The bulk of the composition of the present invention comprises an aqueous/organic carrier or solvent, in the range of 85 to 99.9% w/v of which 1 to 95% w/v is water. The organic portion of the solvent includes methanol, ethanol, isopropanol, polyoxyethylene octyl phenyl ether having the formula $C_8H_{17}C_6H_4(OCH_2CH_2)_n$—OH, where n has an average value of 9 (Octoxynol-9), polyoxyethylene nonyl phenyl ether having the formula $C_9H_{19}C_6H_4(OCH_2CH_2)_nOH$, where n has an average value of 12 (Nonoxynol-12), polypropylene glycol myristyl ether having the formula

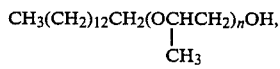

where n has an average value of 3 (PPG-3 Myristyl Ether), and acetylated polyoxyethylene lanolin alcohol with an average ethoxylation value of 9 (Laneth-9 Acetate).

The organic portion comprises about 5 to 99% w/v of the aqueous/organic solvent.

In the preferred embodiment the hair conditioning composition of the present invention comprises about 2 to 5% w/v of an organosilicon quaternary ammonium salt of the above-denoted formula in an aqueous/alcohol solution having a pH of between 8.0 to 10.0, and preferably about pH 9.

The pH of the solution may be adjusted with a cosmetically acceptable alkaline material, preferably with a basic organic compound, such as a primary, secondary and tertiary amine, preferably monoethanolamine.

It is important that the composition be slightly alkaline; alkalinity causes swelling of the hair, thereby allowing penetration of the silane quaternary ammonium compound which is believed to form covalent bonds between the silyl of the compound and the negatively charged surface of hair keratin. To provide for the desired alkalinity, the solution is buffered from about pH 8 to 10, preferably at about pH 9 with a cosmetically acceptable buffering agent, such as monoethanolamine.

While the active ingredient is stable in an aqueous/organic solvent of the present invention, upon the addition of the amine to adjust the pH, the organosilicon quaternary ammonium salt tend to polymerize and precipitate. It is, therefore, preferred to prepare the composition just prior to application to the hair. Alternatively, the organosilicon quaternary ammonium salt is dissolved in the organic portion of the aqueous/organic solvent and packaged, the aqueous phase is prepared separately, its pH is adjusted to the desired alkalinity and packaged. The two phases are mixed together just prior to application to the hair.

In addition to the essential ingredients described above, compositions of the present invention may include optional ingredients to improve cosmetic elegance customarily used in cosmetic preparations. These ingredients include: emollients, such as ethoxylated lanolin ethers and esters, polyethylene glycol diesters, oils such as mineral oil, wheat germ and mink oils; solubilizers, such as fatty alcohol ethoxylates, polyethyleneglycol diesters and alkyl phenol ethoxylates; thickening agents, such as polyethylene glycol and alkyl phenol ethoxylates; opalizing agents, pearlescent agents, coloring agents, preservatives and fragrances.

The foregoing invention will be illustrated by the following examples.

EXAMPLE 1

A hair conditioner having the following composition is prepared:

|  | % w/v |
| --- | --- |
| A. Octadecyldimethyl[3-(trimethoxysilyl) propyl]ammonium chloride | 0.5 |
| Ethyl alcohol | 20.0 |
| Fragrance | 0.2 |
| B. Ethyl alcohol | 10.0 |
| Monoethanolamine to adjust pH to 9 q.s. |  |
| Coloring agent | 0.2 |
| Preservative | 0.1 |
| Water q.s to | 100.0 |

Procedure:

A. The octadecyldimethyl[3-(trimethoxysilyl)propyl]ammonium chloride is added to the ethyl alcohol while mixing, followed by the addition of fragrance with stirring.

B. The preservative and coloring agents are dissolved in ethyl alcohol followed by the addition of water with mixing. The pH of the solution is adjusted to pH 9 with monoethanolamine.

Just prior to use, solutions A and B are mixed until a homogeneous solution is obtained.

EXAMPLE 2

A clear hair conditioner for damaged/dry hair having the following ingredients is prepared:

|   | % w/v |
|---|---|
| A. Octadecyldimethyl[3-(trimethoxy-silyl)propyl]ammonium chloride | 3.0 |
| Nonoxynol-12 | 0.1 |
| Ethyl alcohol | 20.0 |
| Fragrance | 0.2 |
| B. PEG-150 distearate | 2.0 |
| (Polyoxyethylene distearate) |  |
| Ethyl alcohol | 5.0 |
| Laneth-9 acetate | 5.0 |
| Preservative | 0.1 |
| Coloring agent | 0.1 |
| Monoethanolamine to adjust pH to 8.0–9.0 q.s |  |
| Water q.s to | 100.0 |

Procedure:

A. The octadecyldimethyl[3-(timethoxysilyl)propyl]ammonium chloride is added to ethyl alcohol with mixing, followed by the addition of Nonoxynol-12 and fragrance, with mixing.

B. Laneth-9 acetate, PEG-150 distearate, and the preservative are added to ethyl alcohol, with mixing. The coloring agent is dissolved in water and the pH of the water is adjusted to 8.0–9.0 with monoethanolamine. The aqueous phase is then added to the organic phase with mixing.

Prior to use, solutions A and B are mixed together until a homogeneous solution is obtained.

EXAMPLE 3

A pearlescent hair conditioner for damaged/dry hair having the following ingredients is prepared.

|   | % w/v |
|---|---|
| A. Octadecyldimethyl[3-(trimethoxy-silyl)propyl]ammonium chloride | 3.0 |
| PPG-30 cetyl ether | 5.0 |
| (Polyoxypropylene cetyl ether) |  |
| Ethyl alcohol | 20.0 |
| Nonoxynol-12 | 0.1 |
| Fragrance | 0.3 |
| B. Glycol distearate | 2.0 |
| PEG-150 distearate | 2.1 |
| (Polyoxyethylene distearate) |  |
| Wheat germ oil | 1.0 |
| Laneth-9 acetate | 5.0 |
| PEG-8 distearate | 5.0 |
| (Polyoxyethylene distearate) |  |
| Coloring agent | 0.3 |
| Preservative | 0.2 |
| Monoethanolamine to adjust to pH 8.0–9.0 q.s |  |
| Water q.s to | 100.0 |

Procedure:
Analogous to Example 2.

EXAMPLE 4

A clear hair conditioner for normal hair is prepared having the following ingredients:

|   | % w/v |
|---|---|
| A. Stearylmethylbenzyl[3-(trimethoxy-silyl)propyl]ammonium chloride | 3.0 |
| Octoxynol-9 | 0.1 |
| Ethyl alcohol | 20.0 |
| Fragrance | 0.4 |
| B. Ethyl alcohol | 5.0 |
| PEG-150 distearate | 2.0 |
| Laneth-9 acetate | 5.0 |
| Preservative | 0.2 |
| Coloring agent | 0.3 |
| Monoethanolamine to adjust pH to 8.0–9.0, q.s |  |
| Water q.s | 100.0 |

Procedure:
Analogous to Example 2.

EXAMPLE 5

A pearlescent hair conditioner for normal hair is prepared having the following ingredients:

|   | % w/v |
|---|---|
| A. Tetradecyldimethyl[3-(trimethoxy-silyl)propyl]ammonium chloride | 3.0 |
| Octoxynol-9 | 0.1 |
| PPG-30 cetyl ether | 5.0 |
| Ethyl alcohol | 15.0 |
| Fragrance | 0.4 |
| B. PEG-8 distearate | 5.0 |
| Glycol distearate | 2.0 |
| PEG-150 distearate | 2.0 |
| Laneth-9 acetate | 5.0 |
| Ethyl alcohol | 5.0 |
| Coloring agent | 0.2 |
| Preservative | 0.2 |
| Monoethanolamine to adjust pH to 8.0–9.0, q.s |  |
| Water q.s to | 100 |

Procedure:
Analogous to Example 2.

Tests to determine the substantivity of the organosilicon quaternary ammonium salts contained in the formulations of the present invention to hair protein have been conducted using the "Rubine Dye Test". The dye test for determining substantivity of cationic agents to hair demonstrates the degree of attachment of the cationic agent to hair during rinsing with water. Hair treated with a cationic conditioner will gather a rinse-fast stain when subjected to the dye; the coloration gathered on untreated hair is readily rinsed away. The dye complexes with positively charged surfactant residues on the hair forming a stain that resists rinsing from the hair.

PROCEDURE (a) Nine tresses were prepared from a single lot of double bleached hair, each tress being 2 g in weight and 10" in length. Prior to the start of any chemical treatment, each tress was shampooed with a 10% ammonium lauryl sulfate solution, rinsed free of excess detergent and blow dried. Three tresses were ramdomly selected from within this group and submerged for 30 minutes at room temperature in an 80/20 methanol/water solution octadecyldimethyl[3-(trimethoxysilyl)propyl]ammonium chloride (0.3M) buffered at pH 9.0 with monoethanolamine. The silylation step was carried out under mildly alkaline conditions to increase hair swelling and thereby maximize the penetration of the quaternary-silane into the hair. At the same time, the remaining six tresses were submerged in an equivalent volume of solvent. The tresses were removed from their respective solutions and blow dried for one minute to remove excess solvent. Thereafter, the tresses were thoroughly saturated with water pumped from a hand-held sprayer and carefully blow dried at high heat. Three of the blank treated tresses were randomly selected to serve as the controls. The remaining three blank tresses were conditioned with a commercial conditioner according to label directions. All nine tresses were then rinsed with warm tap water to remove excess substrate and carefully re-dried.

The tresses were segregated according to treatment and submerged for 20 minutes at room temperature in 0.5% w/v rubine dye solutions buffered at pH 3.5. The tresses were removed from their respective baths, rinsed with warm tap water to remove excess dye and allowed to drip-dry. Subsequently, the bound rubine dye was removed from the hair by shampooing twice with a 10% ammonium lauryl sulfate solution. The rubine dye/double shampoo cycle was repeated 3 more times. The hair samples were then re-dyed one last time, rinsed and blow dried. At this stage, the tresses were examined for bound rubine dye, first by visual inspection, then by extracting the hair with an aqueous solution of ammonium lauryl sulfate and checking the extract for the color of stripped rubine dye. Finally, after having been rinsed free of surfactant, the tresses were blow dried and examined for qualities looked for in conditioned hair.

(b) The above-described procedure was repeated using nine dark brown virgin hair tresses.

(c) The procedure described in (a) was repeated using nine alkali damaged tresses. The alkali damaged tresses were prepared by submerging virgin hair in a 2% w/v aqueous solution of sodium hydroxide for 30 minutes at room temperature.

RESULTS

After the first dye treatment, all the quaternary-silane and commercial conditioner conditioned tresses showed significant dye pickup whereas the control (blank) tresses showed little or no dye pickup. After the rubine dye initially deposited on the hair was removed by the first double shampoo step, subsequent dye-out treatments demonstrated that only the quaternary-silane treated hair retained the ability to pick up significant amounts of dye. Furthermore, visual inspection showed little change in the intensity of dye retained by quaternary-silane treated hair, even after six more shampooings, indicating no loss of quaternary-silane as a result of washing the hair. In addition, the quaternary-silane treated hair showed greatly reduced static fly-away after combing as compared to the non-treated hair.

These results successfully demonstrate that organosilicon quaternary ammonium halides can be used to impart long term or "permanent" conditioning to all types of hair. The ability of quaternary-silane treated hair to be re-dyed after repeated shampooing clearly demonstrates the substantivity of this silane to hair and that this affinity goes beyond mere ionic attraction. It is postulated that the compound is either convalently bonded to or deposited in the hair fibers in a manner which prevents removal by shampooing.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A hair conditioning composition comprising:
   (a) an effective amount to render long-lasting conditioning effect to hair of an organosilicon quaternary ammonium halide having the formula:

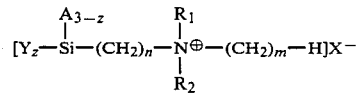

wherein
Y is a hydrolyzable radical selected from the group consisting of alkoxy, halogen or hydroxy;
X is a halogen, sulfate, phosphate or carbonate;
$R_1$ is an alkyl radical of 1 to 4 carbon atoms;
$R_2$ is an aliphatic radical of 1 to 4 carbon atoms or an aromatic radical of 6 to 8 carbon atoms;
A is an aliphatic radical of 1 to 4 carbons or an aromatic radical of 6 to 8 carbons;
n is 1 to 6;
m is 1 to 18 and
z is 2 to 3;
   (b) in an alkaline buffered aqueous/organic vehicle having a pH of about 8.0 to 10.0, said aqueous/organic vehicle comprises:
about 5 to 99% w/v of an organic solvent selected from the group consisting of methanol, ethanol, isopropanol, polyoxyethylene octyl phenyl ether having the formula $C_8H_{17}C_6H_4(OCH_2CH_2)_n$—OH, where n has an average value of 9, polyoxyethylene nonyl phenyl ether having the formula $C_9H_{19}C_6H_4(OCH_2CH_2)_n$—OH, where n has an average value of 12, polypropylene glycol myristyl ether having the formula

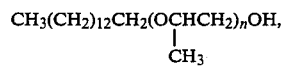

where n has an average value of 3, and acetylated polyoxyethylene lanolin alcohol with an average ethoxylation value of 9;
and about 1 to 95% w/v of water.

2. The hair conditioning composition of claim 1 wherein said hydrolyzable radical is methoxy, ethoxy, propoxy, isopropoxy or butoxy.

3. The hair conditioning compositon of claim 1 wherein said halogen is chlorine, bromine or iodine.

4. A hair conditioning composition comprising:
   (a) about 2.0 to 5.0% w/v of an organosilicon quaternary ammonium salt having the formula:

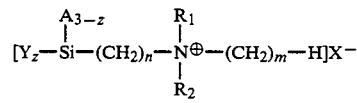

wherein
Y is a hydrolyzable radical selected from the group consisting of alkoxy, halogen or hydroxy;
X is a halogen or anion selected from the group consisting of sulfate, carbonate, or phosphate;
$R_1$ is an alkyl radical of 1 to 4 carbon atoms;

$R_2$ is an aliphatic radical of 1 to 4 carbon atoms or an aromatic radical of 6 to 8 carbon atoms;

A is an aliphatic radical of 1 to 4 carbons or an aromatic radical of 6 to 8 carbons;

n is 1 to 6;

m is 1 to 18; and z is 2 to 3; and (b) up to 98% w/v of an aqueous/alcohol vehicle buffered with a buffering agent having a pH of about 9, said aqueous/organic vehicle comprises:

about 5 to 99% w/v of an organic solvent selected from the group consisting of methanol, ethanol, isopropanol, polyoxyethylene octyl phenyl ether having the formula $C_8H_{17}C_6H_4(OCH_2CH_2)_n$—OH, where n has an average value of 9, polyoxyethylene nonyl phenyl ether having the formula $C_9H_{19}C_6H_4(OCH_2CH_2)_n$—OH, where n has an average value of 12, polypropylene glycol myristyl ether having the formula

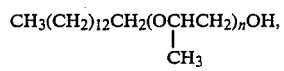

where n has an average value of 3, and acetylated polyoxyethylene lanolin alcohol with an average ethoxylation value of 9 and about 1 to 95% w/v of water.

5. The hair conditioning composition of claim 4 wherein said organosilicon quaternary ammonium salt is octadecyldimethyl[3-(trimethoxysilyl)propyl]ammonium chloride.

6. The hair conditioning composition of claim 4 wherein said organosilicon quaternary ammonium salt is tetradecyldimethyl[3-(trimethoxysilyl)propyl]ammonium chloride.

7. The hair conditioning composition of claim 4 wherein said organosilicon quaternary ammonium salt is N-trimethoxysilylpropyl-N,N,N-trimethylammonium chloride.

8. The hair conditioning composition of claim 4 wherein said organosilicon quaternary ammonium salt is stearylmethylbenzyl[3-(trimethoxysilyl)propyl]ammonium chloride.

9. A hair conditioning composition comprising:

(a) 0.1 to 15.0% w/v of an organosilicon quaternary ammonium salt having the formula:

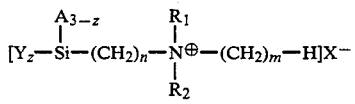

wherein

Y is a hydrolyzable radical selected from the group consisting of alkoxy, halogen or hydroxy, X is a halogen or anion selected from the group consisting of sulfate, carbonate, phosphate;

$R_1$ is an alkyl radical of 1 to 4 carbon atoms;

$R_2$ is an aliphatic radical of 1 to 4 carbon atoms or an aromatic radical of 6 to 8 carbon atoms;

A is an aliphatic radical of 1 to 4 carbons or an aromatic radical of 6 to 8 carbons;

n is 1 to 6;

m is 1 to 18; and z is 2 to 3; and (b) up to 99.9% w/v of an alkaline buffered aqueous/organic vehicle having a pH of about 8.0 to 10.0, said aqueous/organic vehicle comprises:

about 5 to 99% w/v of an organic solvent selected from the group consisting of methanol, ethanol, isopropanol, polyoxyethylene octyl phenyl ether having the formula $C_8H_{17}C_6H_4(OCH_2CH_2)_n$—OH, where n has an average value of 9, polyoxyethylene nonyl phenyl ether having the formula $C_9H_{19}C_6H_4(OCH_2CH_2)_n$—OH, where n has an average value of 12, polypropylene glycol myristyl ether having the formula

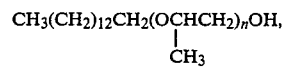

where n has an average value of 3, and acetylated polyoxyethylene lanolin alcohol with an average ethoxylation value of 9;

and about 1 to 95% w/v of water.

10. A method of treating hair to render the same conditioned for an extended time period comprising:
 a. cleaning the hair by shampooing;
 b. applying to the hair an effective amount of the composition of claim 1;
 c. permitting said composition to remain in contact with the hair for a time sufficient to condition said hair;
 d. rinsing the hair free of the composition; and, drying the hair.

11. A method of treating hair to render the same conditioned for an extended time period comprising:
 a. cleaning the hair by shampooing;
 b. applying to the hair an effective amount of the composition of claim 6;
 c. permitting said composition to remain in contact with the hair for a time sufficient to condition said hair;
 d. rinsing the hair free of the composition; and drying the hair.

12. A method of treating hair to render the same conditioned for an extended time period comprising:
 a. cleaning the hair by shampooing;
 b. applying to the hair an effective amount of the composition of claim 4;
 c. permitting said composition to remain in contact with the hair for a time sufficient to condition said hair;
 d. rinsing the hair free of the composition; and, drying the hair.

* * * * *